United States Patent
Koskinen et al.

(10) Patent No.: US 11,360,036 B2
(45) Date of Patent: Jun. 14, 2022

(54) X-RAY FLUORESCENCE ANALYZER, AND A METHOD FOR PERFORMING X-RAY FLUORESCENCE ANALYSIS

(71) Applicant: Outotec (Finland) Oy, Espoo (FI)

(72) Inventors: Tommi Koskinen, Espoo (FI); Antti Pelli, Espoo (FI); Heikki Sipilä, Espoo (FI)

(73) Assignee: Outotec (Finland) Oy, Espoo (FI)

( * ) Notice: Subject to any disclaimer, the term of this patent is extended or adjusted under 35 U.S.C. 154(b) by 0 days.

(21) Appl. No.: 17/049,262

(22) PCT Filed: Apr. 20, 2018

(86) PCT No.: PCT/FI2018/050282
§ 371 (c)(1),
(2) Date: Oct. 20, 2020

(87) PCT Pub. No.: WO2019/202198
PCT Pub. Date: Oct. 24, 2019

(65) Prior Publication Data
US 2021/0255123 A1    Aug. 19, 2021

(51) Int. Cl.
*G01N 23/223* (2006.01)
*G21K 1/06* (2006.01)

(52) U.S. Cl.
CPC .......... *G01N 23/223* (2013.01); *G21K 1/06* (2013.01); *G01N 2223/616* (2013.01); *G21K 2201/062* (2013.01)

(58) Field of Classification Search
None
See application file for complete search history.

(56) References Cited

U.S. PATENT DOCUMENTS

| 3,150,261 A | 9/1964 | Furbee et al. |
| 3,198,944 A | 8/1965 | Furbee |

(Continued)

FOREIGN PATENT DOCUMENTS

| CN | 107424889 A | 1/2017 |
| DE | 137533 A1 | 9/1979 |

(Continued)

OTHER PUBLICATIONS

International Search Report and Written Opinion for International Application No. PCT/FI2018/050282 dated Dec. 5, 2018.

(Continued)

*Primary Examiner* — Hoon K Song
(74) *Attorney, Agent, or Firm* — Andrus Intellectual Property Law, LLP

(57) ABSTRACT

An X-ray fluorescence analyzer includes an X-ray tube for emitting incident X-rays in the direction of a first optical axis. A slurry handling unit is configured to maintain a constant distance between a sample of slurry and the X-ray tube. A first crystal diffractor is located in a first direction from the slurry handling unit and configured to separate a predefined first wavelength range from fluorescent X-rays that propagate into the first direction. The first crystal diffractor is configured to direct the fluorescent X-rays in the separated predefined first wavelength range to a first radiation detector. The first crystal diffractor includes a pyrolytic graphite crystal that has a diffractive surface, which is a simply connected surface. The first radiation detector is a solid-state semiconductor detector.

29 Claims, 7 Drawing Sheets

(56) References Cited

U.S. PATENT DOCUMENTS

| | | | |
|---|---|---|---|
| 3,354,308 A | 11/1967 | Frederick et al. | |
| 2012/0294418 A1 | 11/2012 | Yellepeddi et al. | |
| 2014/0037053 A1* | 2/2014 | Van Haarlem ....... | G01N 23/223 |
| | | | 378/45 |

FOREIGN PATENT DOCUMENTS

| | | | |
|---|---|---|---|
| EP | 1209462 A2 | 5/2002 |
| EP | 3168606 A1 | 5/2017 |
| JP | H07190962 A | 7/1995 |
| WO | 03/048745 A2 | 6/2003 |
| WO | 2013063253 A1 | 5/2013 |
| WO | 2017140938 A1 | 8/2017 |

OTHER PUBLICATIONS

International Preliminary Report on Patentability for International Application No. PCT/FI2018/050282 dated Sep. 4, 2020.
Office Action for corresponding Danish Application No. PA 2020 70772 dated Sep. 16, 2021.
Office Action for corresponding ARIPO Application No. AP/P/2020/012735 dated Feb. 2, 2022.

* cited by examiner

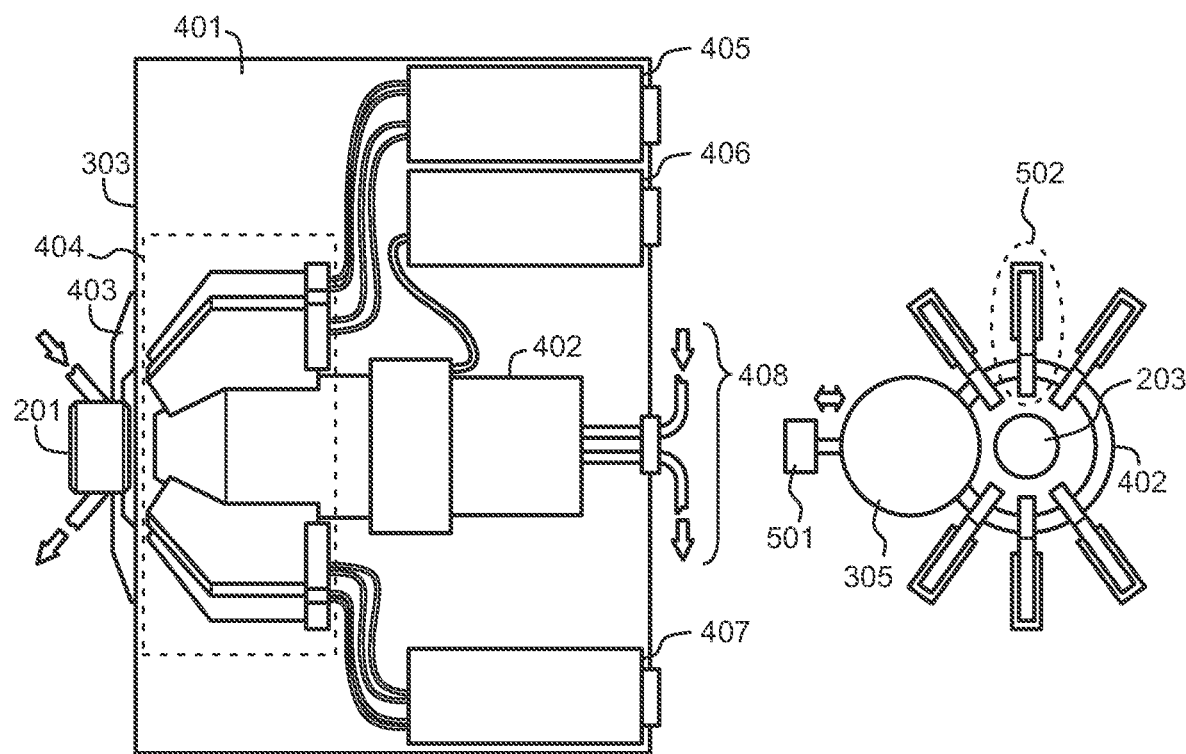
Fig. 4
Fig. 5
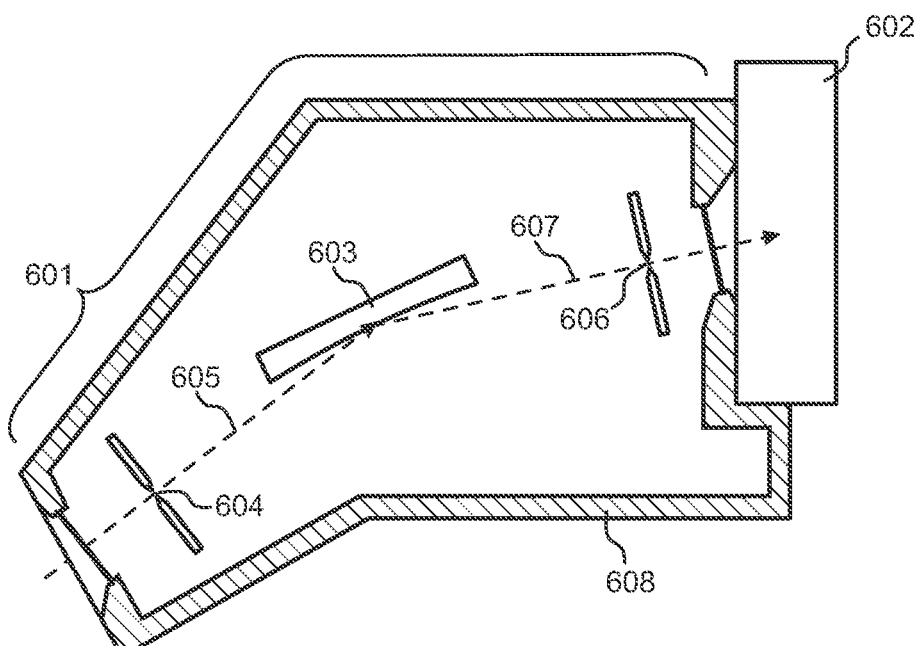
Fig. 6

X-RAY FLUORESCENCE ANALYZER, AND A METHOD FOR PERFORMING X-RAY FLUORESCENCE ANALYSIS

CROSS-REFERENCE TO RELATED APPLICATIONS

This application is the U.S. national stage application of International Application PCT/FI2018/050282, filed Apr. 20, 2018, which international application was published on Oct. 24, 2019, as International Publication WO 2019/202198 A1 in the English language.

TECHNICAL FIELD

The invention relates to the technical field of X-ray fluorescence analysis. In particular the invention relates to the task of detecting relatively small amounts of fluorescent radiation in the presence of significant background radiation.

BACKGROUND

X-ray fluorescence analysis can be used to detect the presence and measure the concentration of elements of interest in a matrix of other elements. For example in mining industry it is important to know, whether a mineral or metal of interest is present in a sample and in which quantities. In order to be applicable in an industrial process, the X-ray fluorescence analysis method should be reasonably accurate even at relatively short exposure times, and possible to implement with robust and mechanically reliable measurement devices.

A particular application of X-ray fluorescence analysis within the mining industry is the analysis of elements of interest in slurries. By definition, a slurry is a water-based suspension of fine, solid particles of crushed and ground ore, in which the dry weight of the solid particles is less than 90 percent, typically 20-80 percent, of the total mass of the sample. The fact that the sample is in the form of slurry places particular requirements for sample handling. For example, it is advantageous to maintain the flow of the sample turbulent, so that its constitution remains evenly mixed and the fractions do not separate from each other. At the same time the measurement geometry should remain as constant as possible in order not to cause unwanted geometry-based variations in measurement results.

The concentrations of elements of interest in the slurry are often very low. For example copper, zinc, lead, and molybdenum need to be measured in concentrations like 0.01 percent or lower, and concentrations of gold to be measured may be in the order of only some ppm, like 1-5 ppm. Such a low concentration makes the measurement difficult, because the intensity of fluorescent radiation from the element of interest is very low, which inevitably increases the effect of statistical errors. When the intensity is low in comparison to other radiation intensities involved, like fluorescent radiation from other, non-interesting elements, overlap with adjacent peaks causes problems. Measurement times cannot be made arbitrarily long, because the slurry comes as a continuous flow from the refining process and is an important online indicator of what is happening in the process. The X-ray fluorescence measurement should be fast enough to detect trending changes in the slurry composition, so that the measurement results could be used to control the refining process in real time.

SUMMARY

It is an objective of the invention to provide an apparatus for performing accurate and reliable X-ray fluorescence analysis of small concentrations of elements in slurry under demanding industrial conditions. Another objective of the invention is to provide such an apparatus at reasonable costs of manufacturing and maintenance. Yet another objective of the invention is that the apparatus is easily adapted for the measurement of any element of interest in the sample.

The foregoing and other objectives are achieved by using a crystal diffractor to separate some of the fluorescent X-rays, so that the crystal diffractor comprises a pyrolytic graphite crystal, the diffractive surface of which is a simply connected surface.

According to a first aspect, an X-ray fluorescence analyzer is provided. The X-ray fluorescence analyzer comprises an X-ray tube for emitting incident X-rays in the direction of a first optical axis, and a slurry handling unit configured to maintain, in the direction of said first optical axis, a constant distance between a sample of slurry and said X-ray tube. The X-ray fluorescence analyzer comprises a first crystal diffractor located in a first direction from said slurry handling unit. Said first crystal diffractor is configured to separate a predefined first wavelength range from fluorescent X-rays that propagate into said first direction, and configured to direct the fluorescent X-rays in the separated predefined first wavelength range to a first radiation detector. The first crystal diffractor comprises a pyrolytic graphite crystal that has a diffractive surface. The diffractive surface of said pyrolytic graphite crystal is a simply connected surface. Said first radiation detector is a solid-state semiconductor detector.

In a possible implementation of the first aspect, the diffractive surface of said pyrolytic graphite crystal is curved in one direction only. This involves the advantage that the crystal is relatively easy and advantageous to manufacture.

In a possible implementation of the first aspect, the first crystal diffractor comprises a substrate to which said pyrolytic graphite crystal is attacked, and a three-dimensional geometrical shape of the entity constituted by said pyrolytic graphite crystal and said substrate is that of a prism, one side face of which is cut away by the curved diffractive surface. This involves the advantage that the mechanical structure of the crystal diffractor can be designed relatively simple.

In a possible implementation of the first aspect, said first radiation detector is one of: a PIN diode detector, a silicon drift detector, a germanium detector, a germanium drift detector. This involves the advantage that the first radiation detector may combine accurate and reliable operation with compact size and robust overall appearance.

In a possible implementation of the first aspect, the first crystal diffractor comprises a first slit on a first optical path between said slurry handling unit and said pyrolytic graphite crystal, and a second optical path between said pyrolytic graphite crystal and said first radiation detector. This involves the advantage that a desired proportion of the fluorescent radiation can be selected.

In a possible implementation of the first aspect, the diffractive surface of said pyrolytic graphite crystal is curved in one direction only, with a radius of curvature in a plane defined by said first and second optical paths, and said first slit is a linear slit oriented perpendicular against said plane. This involves the advantage that manufacturing the crystal diffractor is relatively simple.

In a possible implementation of the first aspect, the diffractive surface of said pyrolytic graphite crystal is curved in two directions, forming a part of a toroidal surface, and said first slit is a curved slit with a first radius of curvature oriented perpendicular against said first optical path. This involves the advantage that the focusing accuracy of the crystal diffractor is relatively good.

In a possible implementation of the first aspect, the diffractive surface of said pyrolytic graphite crystal is curved in two directions, forming a part of a rotationally symmetric surface, the rotational axis of which is in the plane defined by said first and second optical paths, and said first slit is point-like. This involves the advantage that the focusing accuracy of the crystal diffractor is very good.

In a possible implementation of the first aspect, the first crystal diffractor comprises a second slit on said second optical path between said pyrolytic graphite crystal and said first radiation detector; a center point of said diffractive surface, said first slit, and said second slit are located on a Rowland circle the radius of which is R; a radius of curvature of said diffractive surface in the plane defined by said first and second optical paths is 2R; and a radius of curvature of reticular planes in said crystal is 2R; so that the first crystal diffractor has a Johann geometry. This involves the advantage that well-known geometrical relations can be used for the various components.

In a possible implementation of the first aspect, the first crystal diffractor comprises a second slit on said second optical path between said pyrolytic graphite crystal and said first radiation detector; a center point of said diffractive surface, said first slit, and said second slit are located on a Rowland circle the radius of which is R; a radius of curvature of said diffractive surface in the plane defined by said first and second optical paths is R; and the radius of curvature of reticular planes in said crystal is 2R; so that the first crystal diffractor has a Johansson geometry. This involves the advantage that well-known geometrical relations can be used for the various components.

In a possible implementation of the first aspect, R is at most 40 centimeters. This involves the advantage that the physical size of the apparatus can be maintained relatively compact.

In a possible implementation of the first aspect, said first crystal diffractor is enclosed in a casing delimited by a first planar surface and a second planar surface that is parallel to said first planar surface. This involves the advantage that the mechanical structure of the detection channel can be made relatively simple.

In a possible implementation of the first aspect, the X-ray fluorescence analyzer comprises a plurality of other crystal diffractors in addition to said first crystal diffractor, each of said first and other crystal diffractors being located at a respective rotation angle around said first optical axis and each of said first and other crystal diffractors being configured to separate a predefined wavelength range from fluorescent X-rays that propagate into the respective direction, and configured to direct the fluorescent X-rays in the respective separated predefined wavelength range to a respective radiation detector. This involves the advantage that a large number of elements can be analyzed from the sample without changing the physical configuration of the apparatus.

In a possible implementation of the first aspect, said plurality of other crystal diffractors comprises a second crystal diffractor comprising a second crystal, configured to direct the fluorescent X-rays in the respective separated second predefined wavelength range to a respective second radiation detector; said second crystal is of a material other than pyrolytic graphite; and said first and second crystal diffractors are configured to direct to their respective radiation detectors characteristic fluorescent radiation of a same element. This involves the advantage that the measurement can be made more reliable and more readily adaptable to a number of cases.

In a possible implementation of the first aspect, said second crystal is one of: a silicon dioxide crystal, a lithium fluoride crystal, an ammonium dihydrogen phosphate crystal, a potassium hydrogen phthalate crystal. This involves the advantage that sharp wavelength dispersive diffraction can be obtained with the second crystal.

In a possible implementation of the first aspect, said second radiation detector is a gas-filled proportional counter. This involves the advantage that relatively good detection efficiency can be achieved at relatively low manufacturing cost.

In a possible implementation of the first aspect, said element is gold. This involves the advantage that even very low concentrations of a relatively valuable element can be detected.

In a possible implementation of the first aspect, said slurry handling unit is configured to maintain a planar surface of said sample of slurry on a side facing said X-ray tube; said first optical axis is at an oblique angle against said planar surface; said first crystal diffractor is located at that rotational angle around said first optical axis at which said planar surface of said sample covers the largest portion of a field of view of the first crystal diffractor; and said second crystal diffractor is located at another rotational angle around said first optical axis. This involves the advantage that fluorescent radiation can be collected to the first crystal diffractor from as large spatial angle as possible.

In a possible implementation of the first aspect, an energy resolution of said first radiation detector is better than 300 eV at a reference energy of 5.9 keV. This involves the advantage that the detector can provide accurate energy dispersive detection within the relatively wide wavelength range passed by the pyrolytic graphite crystal.

In a possible implementation of the first aspect, the input power rating of said X-ray tube is at least 400 watts. This involves the advantage that a relatively large amount of fluorescent radiation can be generated.

In a possible implementation of the first aspect, the input power rating of said X-ray tube is at least 1 kilowatt, preferably at least 2 kilowatts, and more preferably at least 4 kilowatts. This involves the advantage that an even larger amount of fluorescent radiation can be generated.

In a possible implementation of the first aspect, the optical path between said X-ray tube and said slurry handling unit is direct with no diffractor therebetween. This involves the advantage that a large proportion of the original incident radiation can be utilized, and the X-ray tube can be placed very close to the sample.

In a possible implementation of the first aspect, the X-ray tube comprises an anode for generating said incident X-rays, and said slurry handling unit is configured to maintain a shortest linear distance that is shorter than 50 mm, preferably shorter than 40 mm, and more preferably shorter than 30 mm between said sample (202) of slurry and said anode. This involves the advantage that a large proportion of the original incident radiation can be utilized.

In a possible implementation of the first aspect, said X-ray tube is an X-ray tube of the end window type. This involves the advantage that a short distance between X-ray tube and sample can be realized while simultaneously leaving ample space for detection channels.

In a possible implementation of the first aspect, the X-ray fluorescence analyzer comprises an analyzer body, a front wall of said analyzer body, an opening in said front wall, and a holder for removably holding said slurry handling unit against an outer side of said front wall and aligned with said opening in said front wall. This involves the advantage that the slurry handling unit is easy to remove for servicing.

In a possible implementation of the first aspect, said X-ray tube and said first crystal diffractor are both inside said analyzer body, on the same side of said front wall. This involves the advantage that the structure is robust, and good protection can be obtained against accidentally irradiating anything.

In a possible implementation of the first aspect, the X-ray fluorescence analyzer comprises a filter plate on the optical path between said X-ray tube and said slurry handling unit. This involves the advantage that the spectrum of the incident radiation can be tuned in a suitable way.

In a possible implementation of the first aspect, said filter plate is located closer to said X-ray tube than to said slurry handling unit. This involves the advantage that the filter does not unnecessarily obstruct the field of view of the detection channels.

In a possible implementation of the first aspect, the X-ray fluorescence analyzer comprises a calibrator plate and an actuator configured to controllably move said calibrator plate between at least two positions, of which a first position is not on the path of the incident X-rays and a second position is on the path of the incident X-rays and in a field of view of the first crystal diffractor. This involves the advantage that calibrating can be easily automatized.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings:

FIG. 4 illustrates an example of an X-ray fluorescence analyzer, FIG. 5 illustrates some structural details of an example of an X-ray fluorescence analyzer, FIG. 6 illustrates an example of a crystal diffractor.

DETAILED DESCRIPTION

Figure 1:
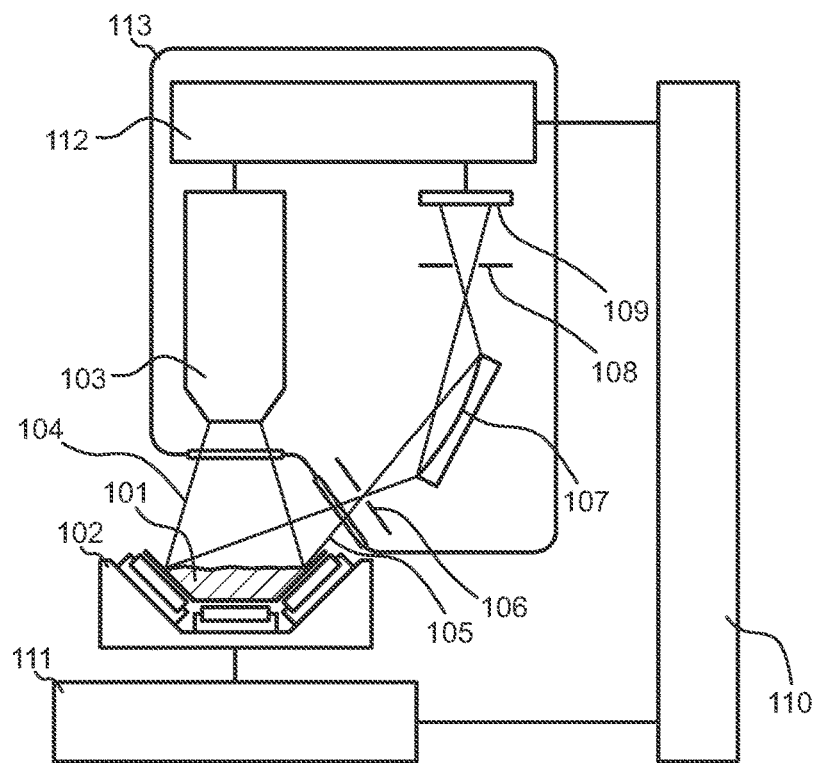
FIG. 1 illustrates a principle of X-ray fluorescence analysis in an industrial process.

FIG. 1 illustrates an example of the principle of using an X-ray fluorescence analyzer in an industrial process. It is typical to industrial processes that the sample to be analyzed may come as a more or less continuous flow of sample material, so that there is a sample handling unit or system that brings the sample to the analysis and takes it away after the analysis. In the schematic illustration of FIG. 1 the sample 101 comes as a flow of sample material on a conveyor 102, which here constitutes the sample handling system. An X-ray source 103 generates a beam 104 of incident X-rays that hit a portion of the sample 101 that is within the field of view of the beam 104. Fluorescent X-rays 105 are emitted in all directions, and some of them are collected to a detection system that in FIG. 1 comprises a first slit 106, a wavelength-dispersive diffractor crystal 107, a second slit 108, and a radiation detector 109. The plant may comprise a control computer system 110 that may control the control subsystems 111 and 112 of the conveyor 102 and the X-ray fluorescence analyzer 113 respectively.

The generation of fluorescent X-rays is a stochastic process by nature, so any analysis that is performed on the basis of received fluorescent X-ray photons is basically the more reliable, the more such photons can be collected. A known way to increase the statistical reliability of an X-ray fluorescence analysis is to lengthen the duration of time that the sample remains illuminated by the incident radiation. If the sample is stationary, this means simply waiting a longer time before the sample is changed. The nature of an industrial process may require however that the sample comes as a constantly moving stream. Even then the concept of a longer measurement time exists in a way, because if the constitution of the sample stream remains essentially constant, accumulating the amounts of detected fluorescent X-ray photons from the moving sample stream for X minutes is essentially the same as keeping a portion of the sample material stationary in the analysis for X minutes.

There are limits, however, to how long the averaging time may be when a constantly moving sample stream is analyzed, because the constitution of the sample stream does change, and these changes may be important and should therefore be noticed. Additionally if the sample comes in the form of a slurry there are other factors that make the situation more complicated, like the requirement that the flow of the slurry should remain turbulent in order to prevent separation of the solid and liquid phases. It is not uncommon that a sample of slurry flows through the slurry handling unit at a rate in the order of 20 liters per minute. An objective of the invention is that reasonably good detection results could be obtained by using averaging times in the order of minutes, like 2 minutes or like 3 to 5 minutes.

In the following, improvements to the X-ray fluorescence analysis through factors like measurement geometry, incident radiation power, selection of diffractor crystal materials, selection of detector types, use of a plurality of detection channels, and advanced utilization of detection results, are therefore considered.

Figures 2, 3:
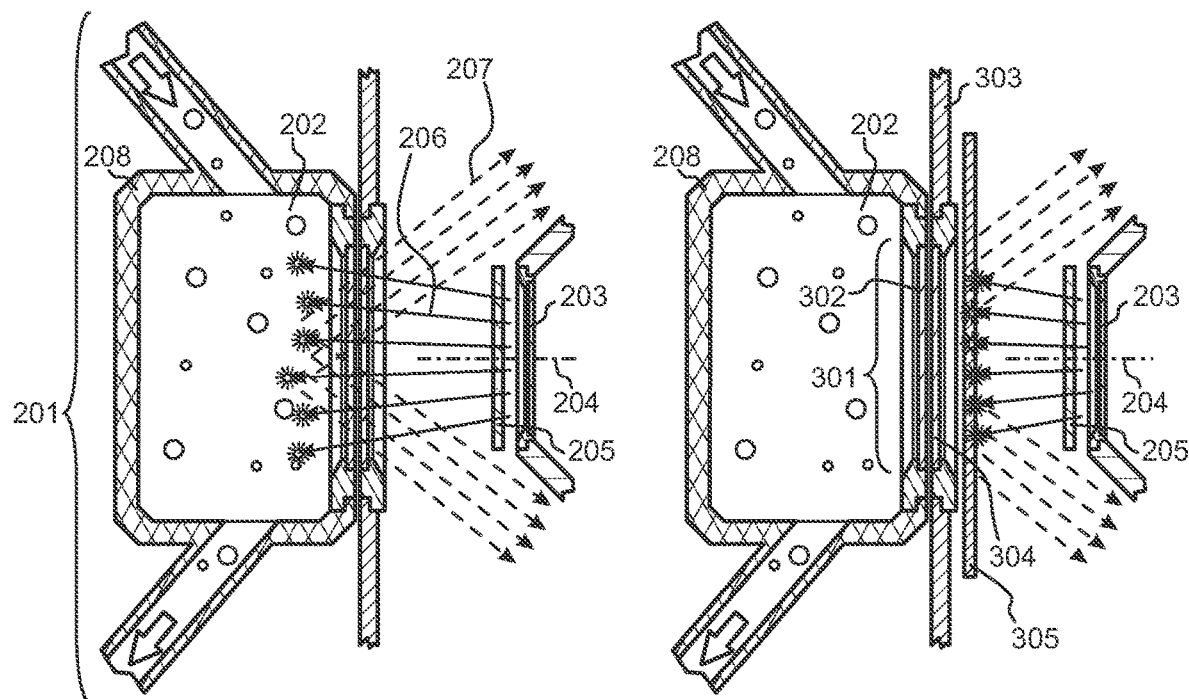
FIG. 2 illustrates a detail of an example of an X-ray fluorescence analyzer.
FIG. 3 illustrates an example of the use of a calibrator plate.

FIG. 2 is a schematic cross section of certain parts of an X-ray fluorescence analyzer. The X-ray fluorescence analyzer comprises an X-ray tube for emitting incident X-rays 206 in the direction of a first optical axis 204. A radiation window 203 of the X-ray tube is seen in FIG. 2. For handling a sample 202 of slurry the X-ray fluorescence analyzer comprises a slurry handling unit 201, which in this case comprises a sample chamber 208 or sample cell equipped with inlet and outlet connections. The exact way in which the sample chamber 208 and its inlet and outlet connections are formed in order to ensure a turbulent flow of the sample 202 inside the chamber is not pertinent to this particular description. As an example, principles explained in the international patent application published as WO2017140938 may be followed. In any case, the slurry handling unit is configured to maintain a constant distance between the sample 202 of slurry and the X-ray tube. The constant distance may be considered for example in the direction of the first optical axis 204.

Keeping the distance constant has the effect that the measurement geometry does not change, at least not with reference to the distance and viewing angle that have an important effect on what proportion of the incident X-rays 206 will hit the sample 202. As such, the apparatus may comprise means for changing the distance, for example by changing a distance at which the X-ray tube is installed. In other words, it is not mandatory that said distance will always remain the same. Merely, it is advantageous for the purposes of straightforward processing of the detection results that the mechanical configuration of the X-ray fluorescence analyzer allows maintaining said distance constant during a measurement, whenever wanted.

FIG. 3 illustrates how the slurry handling unit 201 comprises a sample window 301 in a wall of the sample chamber 208 for allowing X-rays to pass through while keeping the sample 202 of slurry within said sample chamber 208. The sample window 301 is an opening covered by a window foil 302 made of a material that is as transparent to X-rays as possible, while simultaneously being strong enough mechanically to withstand the pressure of, and mechanical wear caused by, the flowing slurry. This way the slurry handling unit is configured to maintain a planar surface of the sample 202 of slurry on a side facing the X-ray tube. In the geometry shown in FIGS. 2 and 3 the first optical axis 204 is perpendicular against said planar surface.

Also shown in FIGS. 2 and 3 is a front wall 303 of an analyzer body, and an opening in said front wall 303. Another window foil 304 covers said opening in the front wall 303. Just like the window foil 302 of the sample window 301 in the sample chamber 208, the other window foil 304 is made of a material that is as transparent to X-rays as possible. The purpose of the other window foil 304 is to protect the inside of the X-ray fluorescence analyzer device against dust, moisture, and other contaminants that may be abundant in its surroundings in an industrial process.

FIG. 2 shows how the incident X-rays 206 that hit the sample 202 give rise to fluorescent X-rays 207. These are originally directed to all directions, but of interest are those fluorescent X-rays 207 that come out of the sample chamber 208 through the sample window 301 and can be collected to one or more detection channels. The location, geometry, and properties of such detection channels are described in more detail later.

Another feature shown in FIGS. 2 and 3 is a filter plate 205 on the optical path between the X-ray tube and the slurry handling unit. A filter plate of this kind is an optional feature. It works as a high-pass filter by attenuating particularly the lowest-energy portion of the X-rays that were originally generated in the X-ray tube. The material and thickness of a filter plate 205, if one is used, can be selected so that it passes those X-rays that are energetic enough to generate fluorescence in the element(s) of interest in the sample 202. It is particularly useful to use a filter of the high-pass type instead of e.g. a primary diffractor that would constitute a band-pass filter, because the high-pass filter will pass a wide range of more energetic incident X-rays, which are then available for generating fluorescent X-rays in a number of elements of interest simultaneously.

If a filter plate 205 is used, it is advantageous to place it closer to the X-ray tube than to the slurry handling unit. The filter plate 205 can be even attached to the X-ray tube, so that it is very close to the radiation window 203 of the X-ray tube. If the filter plate 205 is additionally dimensioned in the transverse direction so that it is only little larger, or not larger at all, than the radiation window 203, it can be ensured that the filter plate 205 does not unnecessarily cover any of the field of view that would otherwise be available for the detection channels. The thickness of the filter plate 205 may be in the order of a millimeter or even less, so the use of a filter plate does not increase the overall distance between the X-ray tube and the sample to any significant extent.

Another feature that is shown in FIGS. 2 and 3 is a calibrator plate 305 that can be controllably and selectively brought into a position in which it is on the path of the incident X-rays 206 and in a field of view of the detection channels that are used to receive the fluorescent X-rays 207. A calibrator plate 305 has a very exactly known composition, so it can be used to calibrate the detection channels from time to time. If the calibration process should be automatized, the X-ray fluorescence analyzer may be equipped with an actuator that is configured to controllably move the calibrator plate 305 between at least two positions, one of which is the position shown in FIG. 3 and the other is a position that is not on the path of the incident X-rays 206.

FIG. 4 illustrates an example of an X-ray fluorescence analyzer according to an embodiment of the invention. It comprises an analyzer body 401 that acts as the basic support and protective structure. The front wall 303 of the analyzer body is visible on the left in FIG. 4. As explained earlier with reference to FIGS. 2 and 3, there is an opening in the front wall 303 for the incident X-rays generated by an X-ray tube 402 to pass through. A holder 403 is provided for holding the slurry handling unit 201 against an outer side of the front wall 303, aligned with said opening in the front wall 303.

In an advantageous embodiment the holder 403 may be configured to hold the slurry handling unit 201 removably against the front wall. The holder 403 may comprise for example hinges that allow turning the slurry handling unit 201 to the side, or a bayonet mount that allows quickly detaching the slurry handling unit 201 from the front wall 303, so that the window foils described above with reference to FIGS. 2 and 3 are exposed. This allows relatively straightforward inspecting and servicing of those parts that are critical for the propagation of both the incident X-rays and fluorescent X-rays. The solid particles in the slurry may cause significant wear to the inside of the window foil 302 of the sample window 301 (see FIG. 3), so it is advantageous to equip the sample window 301 with a mechanism that allows replacing the window foil 302 when necessary.

A portion of the X-ray fluorescence analyzer that is marked with a dashed rectangle 404 in FIG. 4 is shown from the direction of the optical axis of the X-ray tube 402 in FIG. 5. This illustration shows an example of how an actuator 501 can be provided for controllably moving the calibrator plate 305 between the two positions. In the first position, which is shown in FIG. 5, the calibrator plate 305 is not on the path of the incident X-rays that come out of the radiation window 203 of the X-ray tube. In the second position the calibrator plate 305 would be essentially concentric with the radiation window 203 in FIG. 5.

FIGS. 4 and 5 also show how one or more detection channels 502 may be provided. The structure and operation of a detection channel will be described in more detail later in this text. FIGS. 4 and 5 illustrate a positioning principle, according to which each of the detection channels is located at a respective rotation angle around the optical axis of the X-ray tube 402. When the optical axis of the X-ray tube 402 is perpendicular against the planar surface of the sample (which is defined by the sample window that is a part of the slurry handling unit 201), this way of placing the detection channels allows arranging an exactly equal field of view for all detection channels.

Other features shown in FIG. 4 are the provision of electronics boxes 405, 406, and 407 inside the analyzer body 401 for each of the detection channels and for the X-ray tube 402, as well as the provision of a cooling water circulation 408 for the X-ray tube 402.

FIG. 6 is a schematic illustration of certain parts of what was called a detection channel above. Major features of the detection channel of FIG. 6 are a crystal diffractor 601 and a radiation detector 602. As its name indicates, the crystal diffractor 601 comprises a crystal 603, which may be called the diffractor crystal or just crystal for short. The crystal 603 is the wavelength-dispersive component of the crystal diffractor 601. A first slit 604 may be provided on a first optical path 605 between the slurry handling unit (not shown in FIG. 6) and the crystal 603, and a second slit 606 may be provided on a second optical path 607 between the crystal 603 and the radiation detector 602. Since the diffractive properties of the crystal 603 for X-rays are highly dependent on wavelength of the X-rays, this kind of an arrangement can be used to separate a particular wavelength range from that portion of the fluorescent X-rays that were originally emitted into that direction in which this particular crystal diffractor is located. Reference designator 608 illustrates a casing that encloses the crystal diffractor 601, offering structural support for all of its components.

Figure 7:
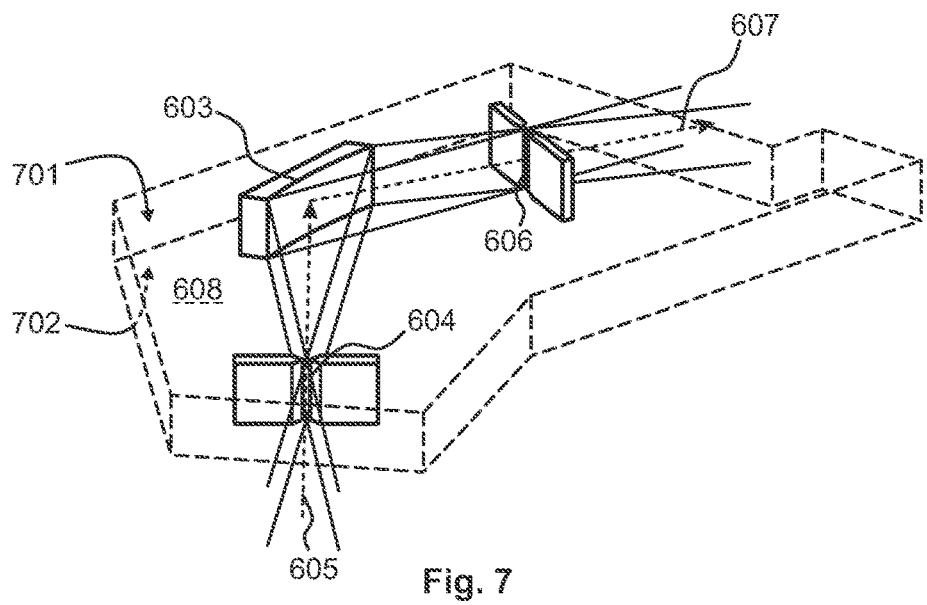
FIG. 7 illustrates some geometrical aspects of a crystal diffractor.

FIG. 7 illustrates an example of a crystal diffractor in an axonometric projection. The crystal diffractor is thought to be located in a first direction from a slurry handling unit (not shown in FIG. 7), so that the first optical path 605 represents the nominal direction of that portion of fluorescent X-rays that are received in this crystal diffractor. The first 604 and second 606 slits are formed between the respective limiter pieces, and the second optical path 607 represents the nominal direction of the diffracted fluorescent X-rays that are directed to the radiation detector (not shown in FIG. 7). The crystal diffractor is enclosed in a casing 608 delimited by a first planar surface 701 and a second planar surface 702 that is parallel to said first planar surface 701.

The mechanical structure described here is advantageous, because the planar surfaces 701 and 702 offer a support to which the internal parts of the crystal diffractor can be attached in a relatively simple way.

Diffraction of X-rays in a crystal is governed by Bragg's law, which ties the diffraction angle to the distance between reticular planes. Conventional crystal diffractors have used crystals of e.g. silicon dioxide, lithium fluoride, ammonium dihydrogen phosphate, or potassium hydrogen phthalate, because sufficiently large monocrystalline pieces of these materials can be manufactured relatively easily at the required accuracy in the desired shapes. However, it has been found that while the wavelength selectivity of such conventional crystals is relatively good, the efficiency at which incoming X-rays are diffracted is relatively poor.

Pyrolytic graphite is an alternative material for producing the crystal for a crystal diffractor. Pyrolytic graphite is a general term that refers to materials that were manufactured from organic compounds containing planar structures like benzene rings, by subjecting them to high temperatures, causing essentially only the carbon atoms of the structure to remain. The original planar molecular structures cause the pyrolytic graphite to exhibit a highly ordered microscopic structure, for which reason it is often referred to as HOPG (highly oriented pyrolytic graphite) or HAPG, in which the latter refers to a slightly different method of synthesizing the material. Pyrolytic graphite is often not monocrystalline in the same sense as the more conventional crystal materials mentioned above, but polycrystalline. In order to maintain consistency with the established wording on this technical field it is nevertheless practical to refer to the diffractor element made of pyrolytic graphite as the "crystal". In the following description the term "HOPG crystal" will be used.

The efficiency of a HOPG crystal as a diffractor of fluorescent X-rays has been found to be significantly better than that of the conventional materials of diffractor crystals. In other words, a significantly higher proportion of X-rays that hit a HOPG crystal are actually diffracted than with the conventional crystal materials. However, the polycrystalline nature of pyrolytic graphite means that not all reticular planes are as exactly oriented as in e.g. monocrystalline silicone dioxide. This in turn means that the wavelength selectivity of a HOPG crystal in a crystal diffractor is not very exact: fluorescent X-rays that get diffracted into a particular direction represent a range of wavelengths around the nominal wavelength that according to Bragg's law would be diffracted into that direction, and this range is significantly wider than in X-rays diffracted by the conventional crystal materials.

The less accurate wavelength selectivity of the HOPG crystal is not, however, a serious drawback because it can be balanced with other factors in the design of the X-ray fluorescence analyzer. One possible approach is to use a solid-state semiconductor detector as the radiation detector 602 to which the fluorescent X-rays in the separated wavelength range are directed from the HOPG crystal. The radiation detector 602 may be for example a PIN diode detector, a silicon drift detector, a germanium detector, or a germanium drift detector. Contrary to for example gas-filled proportional counters, the energy resolution of solid-state semiconductor detectors can be made more accurate. It is customary to express the energy resolution of a detector of X-rays at a reference energy of 5.9 keV. A solid-state semiconductor detector of the kind mentioned above may have an energy resolution better than 300 eV at said reference energy of 5.9 keV.

Combining the use of a HOPG crystal in the crystal diffractor 601 to the use of a solid-state semiconductor detector as the radiation detector 602 may result in an advantageous situation in which the crystal diffractor 601 is configured to separate a predefined first wavelength range from fluorescent X-rays 207 that propagate into the direction at which the crystal diffractor 601 is located (with reference to the slurry handling unit 201), and configured to direct the fluorescent X-rays in the separated predefined first wavelength range to the radiation detector 602 that is a solid-state semiconductor detector. The good energy resolution of the solid-state semiconductor detector is then used to produce a measurement result that indicates an energy spectrum of the fluorescent X-rays in the separated predefined first wavelength range. From said energy spectrum, and possibly using other measurements as support, the amount of fluorescent X-rays from the element of interest can be determined with relatively good accuracy.

Figure 8:
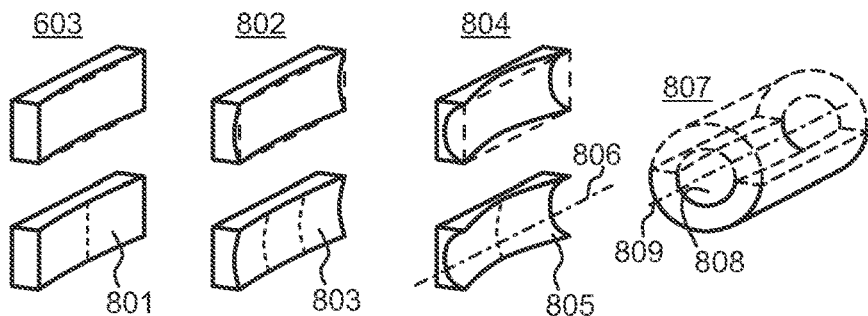
FIG. 8 illustrates some shapes of diffractor crystals.

The geometrical form of the diffractive surface of the HOPG crystal is another factor to consider in the design of the X-ray fluorescence analyzer. FIG. 8 illustrates some examples of geometrical forms. Here it may be noted that exactly speaking the "crystal" is only a thin layer of crystalline (monocrystalline, as in the case of silicon dioxide for example, or polycrystalline, as in the case of HOPG, for example) material that constitutes the actual diffractive surface. The crystal diffractor comprises a substrate to which the crystalline material is attached. Examples of substrate materials are for example glass and aluminum, but the substrate material could also be iron or any other such material that is not prone to causing unwanted, interfering fluorescent radiation by itself. The crystalline material may be attached to an appropriately formed surface of the substrate through for example Van der Waals forces. Alternatively the crystalline material could be grown directly upon the appropriately formed surface of the substrate, or some other suitable attachment method like glue could be used.

Together the substrate and the crystalline material constitute a three-dimensional entity, and examples of these entities are seen in FIG. 8. In order to maintain consistency with the established parlance on this technical field, these entities are called crystals in this text despite of the slight inaccuracy of this term that is explained above. The term diffractive surface refers to the external, exposed surface of the crystalline material at which the diffraction of X-rays takes place; strictly speaking the diffraction of X-rays takes place at the reticular planes inside the crystalline material close to the surface that is here called the diffractive surface.

A feature common to crystal 603, crystal 802, and 804 in FIG. 8 is that a three-dimensional geometrical shape of the entity constituted by the HOPG crystal and the substrate is that of a prism, one side face of which is cut away by the curved diffractive surface. The imaginary form of the prism is shown with dashed lines in the upper-line illustrations of these three crystals.

The lower-line illustrations of the same crystals in FIG. 8 shows how the way in which the diffractive surface is curved is different in all three cases. In crystal 603 the diffractive surface 801 is curved in one direction (longitudinal direction) only. In other words, if an imaginary transverse line was drawn across the diffractive surface 801 at any location, like the dashed line shown in FIG. 8 for example, it would always be straight. A particular advantage of this kind of a crystal is that it is relatively easy to manufacture. Comparing to FIGS. 6 and 7 it can be seen that the radius of curvature of the diffractive surface 801 lies in a plane defined by the first 605 and second 606 optical paths. This plane is also parallel to the planar surfaces 701 and 702.

In crystal 802 the diffractive surface 803 is curved in two directions (longitudinal and transverse), forming a part of a toroidal surface. This means that if a transverse arc was drawn across the diffractive surface 803 at any location, like the two dashed arcs shown in FIG. 8 for example, each of these transverse arcs would be identical to each other. Although this geometrical form may be somewhat more complicated to manufacture at the required accuracy than that of surface 801 on the left, it involves the advantage that it focuses the diffracted X-rays more accurately.

In crystal 804 the diffractive surface 805 is curved in two directions (longitudinal and transverse), but in a different way than surface 803 in the middle. The diffractive surface 805 forms a part of a rotationally symmetric surface, the rotational axis 806 of which is in the plane defined by the optical paths of the incoming and diffracted X-rays. This means that if a transverse arc was drawn across the diffractive surface 805, like the dashed arc in FIG. 8 for example, the radius of curvature of such a transverse arc would be different depending on at which longitudinal location it was drawn. In FIG. 8 it can be seen that the dashed arc in the middle is not as pronouncedly curved as the arc-formed edges seen at the ends of the crystal 804. This is because the dashed arc is located further away from the rotational axis 806 than the arc-formed edges at the ends of the crystal.

Mathematically speaking, a rotationally symmetric surface is formed when a continuous curve is rotated about the rotational axis. The form of said continuous curve defines, how far from the rotational axis each point of the surface will be, and what properties the surface may have. One example of a curve that could be used to form the diffractive surface 805 in FIG. 8 is a section of a logarithmic spiral. Although this kind of a surface is more complicated to manufacture than those introduced above as surfaces 801 and 803, a rotationally symmetric surface made with a section of a logarithmic spiral involves the inherent advantage that it provides very accurate focusing of diffracted X-rays.

A feature that is common to all diffractive surfaces 801, 803, and 805 in FIG. 8 is that in topological sense they are simply connected surfaces. A simply connected surface is one that is path-connected (i.e. any two points on the surface can be connected with a path that belongs wholly to said surface), and additionally any loop-formed path can be continuously contracted to a point so that also all intermediate forms of the contracted loop belong wholly to said surface.

An intuitive description of a simply connected surface is that it does not have holes. As such, it could be possible to drill a small hole through any of the diffractive surfaces 801, 803, or 805 in FIG. 8 without changing their properties as diffractors more than just by decreasing the surface area by the amount that was drilled away. For this reason it is defined here that the requirement of the surface being simply connected in topological sense is to be interpreted to concern the general form of the surface: under such an interpretation a small hole in the surface does not yet mean that it would not be simply connected. Another definition of how the requirement of being simply connected should be interpreted is as follows: if the crystal is "lying on its side" as in FIG. 8 (i.e. a main radius of curvature, which defines the longitudinal curvature between the ends of the crystal, is in a horizontal plane; so that the diffractive surface is generally vertically oriented), any imaginary horizontal line would pierce the diffractive surface at one point at the most. A surface is a simply connected if it fits at least one of these intuitive descriptions.

On the right in FIG. 8 a crystal 807 is shown as a comparative example. The diffractive surface 808 of the crystal 807 is curved in two directions (longitudinal and transverse), forming a complete rotationally symmetric surface, the rotational axis 809 of which could be in a plane defined by the optical axes of the incoming and diffracted X-rays. The curve, the rotation of which about the rotational axis 809 defined the form of the diffractive surface 808, may be for example a section of a logarithmic spiral. It is obvious that the diffractive surface 808 is not simply connected in topological sense, because no closed curve that circumnavigates the bore of the surface can be contracted to a point. Crystals of this kind are relatively complicated to manufacture, but they can be used, together with suitable shields (not shown in FIG. 8) that block the propagation of direct, not diffracted X-rays, to collect fluorescent radiation from a larger spatial angle than those with a simply connected surface like 801, 803, or 805.

The geometric shape and the resulting optical properties of the diffractive surface may have an effect on how other parts of the crystal diffractor should be designed. Above it was explained how the crystal diffractor 601 may comprise a first slit 604 on the first optical path 605 between the slurry handling unit 201 and the (pyrolytic graphite) crystal, and how there is the second optical path 607 between the (pyrolytic graphite) crystal and the radiation detector 602. If the diffractive surface 801 of said (pyrolytic graphite) crystal 603 is curved in one direction only, with a radius of curvature in a plane defined by said first 605 and second 607 optical paths, it is advantageous to make said first slit 604 a linear slit oriented perpendicular against said plane, like in FIG. 7. If the diffractive surface 803 of said (pyrolytic graphite) crystal 802 is curved in two directions, forming a part of a toroidal surface, it is advantageous to make said first slit a curved slit with a radius of curvature oriented perpendicular against said first optical path. If the diffractive surface 805 of said (pyrolytic graphite) crystal 804 is curved in two directions, forming a part of a rotationally symmetric surface, the rotational axis 806 of which is in the plane defined by said first and second optical paths, it is advantageous to make said first slit point-like.

If a second slit 606 is used on the second optical path 607, similar considerations may apply. However, it should be noted that the second slit is not always necessary: its use is related to attenuating background and scattered radiation particularly with diffractor crystals that are highly wavelength-selective. Taken that the wavelength selectivity of a HOPG is not that high, the additional advantage gained with a second slit is relatively small.

Figures 9, 10:
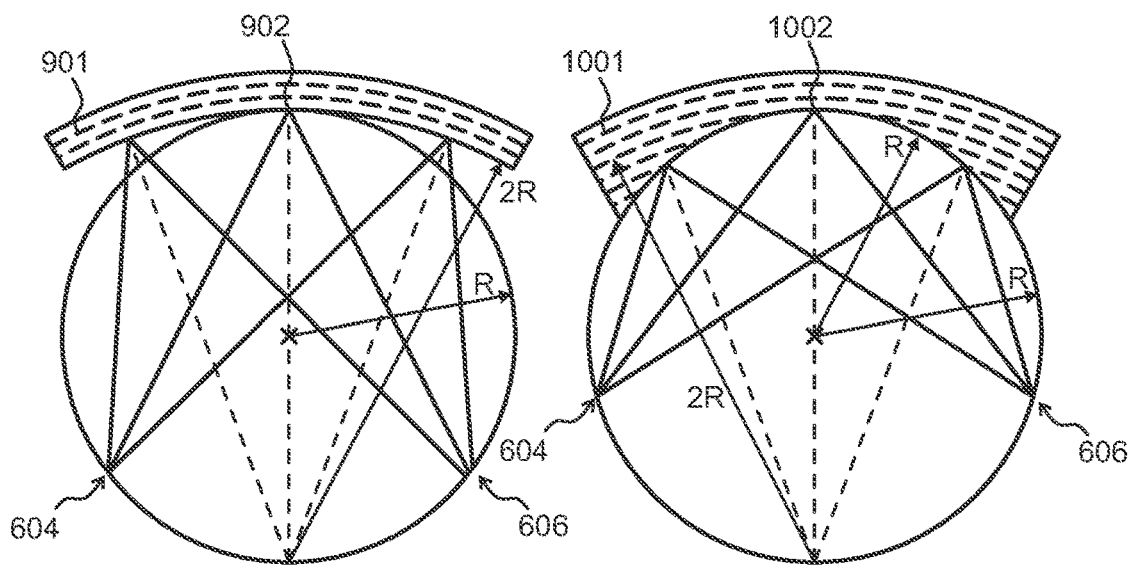
FIG. 9 illustrates an example of a radiation propagation geometry.
FIG. 10 illustrates another example of a radiation propagation geometry.

If a second slit is used on the second optical path 607 between the (pyrolytic graphite) crystal 603, 802, 804 and the first radiation detector, the geometry of the crystal diffractor may follow for example the principle of a Johann geometry or a Johansson geometry. These are illustrated in FIGS. 9 and 10 respectively. In FIG. 9 a center point 902 of said diffractive surface, said first slit 604, and said second slit 606 are located on a Rowland circle the radius of which is R. A radius of curvature of said diffractive surface in the plane defined by said first and second optical paths is 2R, and a radius of curvature of reticular planes 901 in said crystal is 2R. This means that the first crystal diffractor has a Johann geometry. In FIG. 10 a center point 1002 of said diffractive surface, said first slit 604, and said second slit 606 are similarly located on a Rowland circle the radius of which is R. However, here a radius of curvature of said diffractive surface in the plane defined by said first and second optical paths is R, and the radius of curvature of reticular planes 1001 in said crystal is 2R, so that the first crystal diffractor has a Johansson geometry.

In order to maintain a compact size of the crystal diffractor it is advantageous if the magnitude of R can be kept relatively small. As an example, R may be at most 40 centimeters.

FIGS. 11 to 14 are schematic illustrations of spectra of fluorescent X-rays in certain cases. The spectra are typically expressed as detected counts at each photon energy. In practice the detector that produces the counts has a certain energy resolution that defines, how close to each other the energies of two photons may be so that the detector is capable of producing two different kinds of output signals. Signal processing is used to classify the received X-ray photons into energy bins of finite width, and the counts are given per energy bin. The more accurate the detector resolution, the narrower (in terms of energy units) the energy bins can be made.

Figure 11:
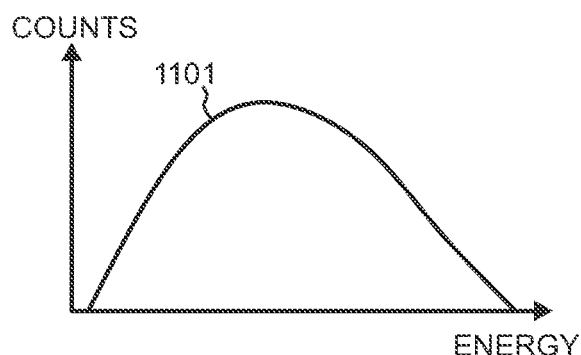
FIG. 11 illustrates an example of a radiation spectrum.
Figure 12:
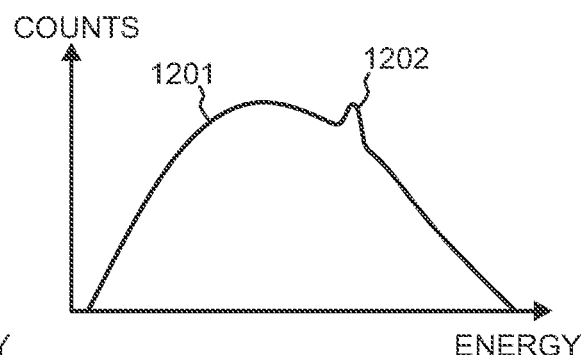
FIG. 12 illustrates another example of a radiation spectrum.

In FIG. 11 the graph 1101 is smooth without any visible peaks or spectral holes. Such a spectrum is rarely obtained in practice, but it illustrates a situation in which only background and randomly scattered radiation is received, without any characteristic peaks of elements of interest. In FIG. 12 the graph 1201 is otherwise the same, but there is a characteristic peak 1202 of an element of interest. The problem is that the concentration of the element of interest in the measured sample is so small that the height of the characteristic peak 1202 is low with respect to the general level of the spectrum at the same energy range. Thus even if a relatively large number of photons are observed in that energy range, relatively few of them are actually fluorescent photons from the element of interest.

Figure 13:
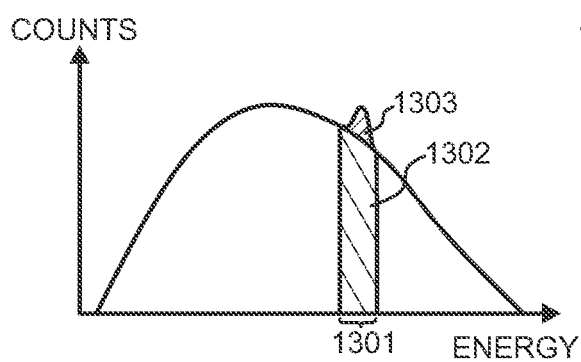
FIG. 13 illustrates another example of a radiation spectrum.

The energy of a photon is inversely proportional to its wavelength, so when the wavelength selectivity of various diffractive crystals has been considered above, energy selectivity could be considered quite as well. FIG. 13 illustrates schematically what the radiation detector of a crystal diffractor equipped with a HOPG crystal could receive. The energy range 1301 of fluorescent X-rays that the HOPG crystal would direct to said radiation detector is relatively wide, which is a direct result of the relatively modest wavelength selectivity of the HOPG crystal. At the same time, however, the diffraction efficiency of the HOPG crystal is relatively good. Thus the radiation detector would receive a significant proportion of the photons falling within the two hatched areas in FIG. 13. Of these, the photons belonging to the first hatched area 1302 are background and scattered photons, while the photons belonging to the second hatched area 1303 are actual fluorescent photons from the element of interest.

Figure 14:
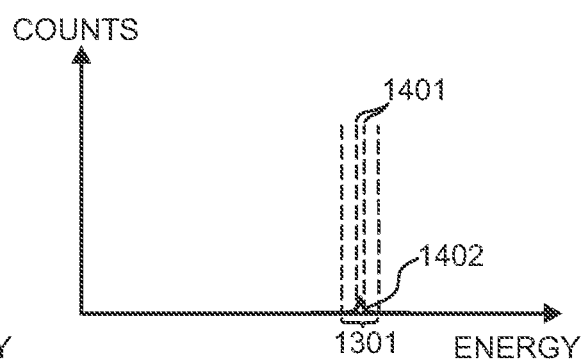
FIG. 14 illustrates another example of a radiation spectrum.

FIG. 14 illustrates schematically what the radiation detector of a crystal diffractor equipped with a silicon dioxide (or other conventional) crystal could receive in the same situation. The energy range 1401 of fluorescent X-rays that the conventional crystal would direct to its radiation detector is relatively narrow, which is a direct result of the relatively good wavelength selectivity of the conventional crystal. At the same time, however, the diffraction efficiency of the conventional crystal is lower than that of a HOPG crystal. Thus the radiation detector would only receive a limited proportion of the photons that actually originated from the element of interest in the sample (see hatched area 1303 in FIG. 13). The small peak 1402 in FIG. 14 represents these fluorescent X-rays, which will actually be detected in this case.

One factor to consider in the design of the X-ray fluorescence analyzer is the possibility to use differently equipped detection channels. Here "differently equipped"

means primarily the selection of the diffractor crystal and the selection of the radiation detector.

Figure 15:
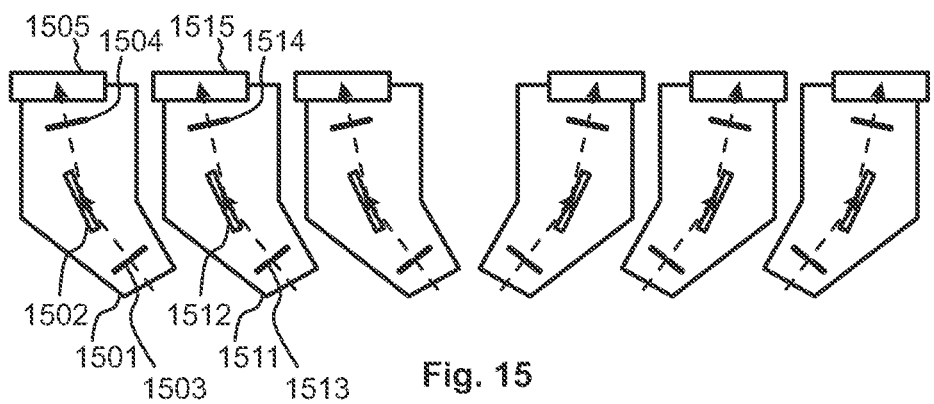
FIG. 15 illustrates a plurality of detection channels.

FIG. 15 illustrates schematically how an industrial X-ray fluorescence analyzer for analyzing samples of slurry may comprise a plurality of detection channels. The detection channels are shown in a straight line in FIG. 15 because the representation is schematic. In practice they could be located for example in a rotationally symmetric manner around the X-ray tube like in FIGS. 4 and 5, each with a field of view directed towards the slurry handling unit of the X-ray fluorescence analyzer.

The X-ray fluorescence analyzer comprises a first crystal diffractor 1501 located in a first direction from said slurry handling unit, said first crystal diffractor 1501 comprising a first crystal. A first radiation detector 1505 is configured to detect fluorescent X-rays diffracted by said first crystal 1502 at a first energy resolution. The X-ray fluorescence analyzer comprises a second crystal diffractor 1511 located in a second direction from said slurry handling unit, said second crystal diffractor comprising a second crystal 1512. A second radiation detector 1515 is configured to detect fluorescent X-rays diffracted by said second crystal 1512 as a second energy resolution.

As a first assumption it may be assumed that the first crystal 1502 is a pyrolytic graphite (HOPG) crystal, and said second crystal 1512 is of a material other than pyrolytic graphite, like silicon dioxide, lithium fluoride, ammonium dihydrogen phosphate, or potassium hydrogen phthalate. Also as a first assumption it may be assumed that the first and second crystal diffractors are configured to direct to their respective radiation detectors characteristic fluorescent radiation of a same element. In other words, the two detection channels are equipped differently, but they both aim at detecting the presence and concentration of the same element in the sample of slurry.

As such, configuring a crystal diffractor to direct to its radiation detector characteristic fluorescent radiation of a particular element is typically done by 1) selecting a crystal with a particular distance between its reticular planes, 2) selecting the curvature of the crystal and the reticular planes, and 3) selecting the angle and distance values of the crystal and the slit(s) so that X-rays of just a particular wavelength range will reach the detector, said particular wavelength range including the desired characteristic peak of the element of interest. The element of interest may have several characteristic peaks, so saying that the two detection channels are configured for measuring characteristic fluorescent radiation of the same element does not necessarily mean that they would be configured for measuring the same characteristic peak, although that is not excluded either.

If the two detection channels are configured for measuring the same characteristic peak, the measurement results they produce may resemble those in FIG. 13 (for the channel with the HOPG crystal) and 14 (for the channel with the other crystal). The task of finding out the actual concentration of the element of interest may be described in the form of a method, for example as follows.

The method is aimed at performing X-ray fluorescence analysis, and comprises irradiating a sample of slurry with incident X-rays and receiving fluorescent X-rays from the irradiated sample. Due to the measurement geometry, a first portion of the fluorescent X-rays will be directed to the first detection channel, and a second portion of the fluorescent X-rays will be directed to the second detection channel. The method comprises separating first 1301 and second 1401 predefined wavelength ranges from respective first and second portions of said received fluorescent X-rays with respective first 1501 and second 1511 crystal diffractors. Said first wavelength range 1301 and said second wavelength range 1401 both include characteristic fluorescent radiation of a same element. Additionally said first wavelength range 1301 is at least twice as wide as said second wavelength range 1401.

The method comprises detecting the fluorescent X-rays in said first and second separated wavelength ranges with respective first 1505 and second 1515 radiation detectors. The energy resolution of said first radiation detector 1505 is better than 300 eV at a reference energy of 5.9 keV. Thus the method comprises producing respective first and second detection results. The method comprises calculating a concentration of said element in said sample from at least one of said first and second detection results.

Here "at least one" emphasizes the fact that not all detection results are best dealt with in equal manner. Very much depends on the sample. In some samples the concentration of the element of interest may be relatively large, resulting in a relatively large number of detected fluorescent photons even in the second radiation detector 1515 despite the modest diffraction efficiency of the second crystal 1512. In some other case the concentration of the element of interest may be so small that only a very small and vague peak is visible within the second wavelength range 1401. In some cases the first wavelength range 1301 may appears to be relatively clean from any interfering radiation, while some other sample may contains significant amounts of some other element, the characteristic peak of which is so close that it comes visible and even dominant in the first wavelength range 1301 but not in the second wavelength range 1401.

In general the calculating may comprise calculating a combined intensity of background radiation and fluorescent X-rays from others than said element using at least one of the first and second detection results. The method may then comprise subtracting, from the total intensity detected in a wavelength range containing said characteristic peak of fluorescent X-rays of an element to be measured in said sample, the calculated combined intensity of background radiation and fluorescent X-rays from other elements than said element of interest in said sample. The method may then comprise providing the result of said subtracting as the calculated intensity of said characteristic fluorescent X-ray peak.

The calculating may comprise analyzing from said first and second detection results whether the influence of a characteristic peak from another element on the first detection result is larger than a predetermined threshold. If said analyzing shows that the influence of said characteristic peak from said other element on the first detection result is larger than said predetermined threshold, the method may comprise calculating said concentration of said element in said sample from said second detection result. If, on the other hand, said analyzing shows that the influence of said characteristic peak from said other element on the first detection result is not larger than said predetermined threshold, the method may comprise calculating said concentration of said element in said sample from said first detection result.

Another possibility is to form specific models for each measurement channel per sample line, using calibration samples. The measurement channel to be used for the actual measurements of that sample line is then selected on the basis of which of them gives the most accurate calibration.

The element of interest may be gold, because gold is valuable and because reasonably effective methods exist for extracting it even from flows of slurry where it appears in very low concentrations. There are other elements, interfering characteristic peaks of which may or may not be present and may appear very close to one of gold. If significant amounts of such interfering elements are present in the sample, the detection channel with the HOPG crystal may give relatively inaccurate and unreliable results, at least if used alone.

Intermediate forms of these two extreme cases can be presented, in which the contribution of the first and second detection results are taken into account in various ways. The decision about which calculating method is selected can be made for example with an artificial intelligence algorithm that compares the first and second detection results to previously obtained comparable results and to some kind of evaluation data about how the various available calculation methods performed with said comparable results.

Figure 16:
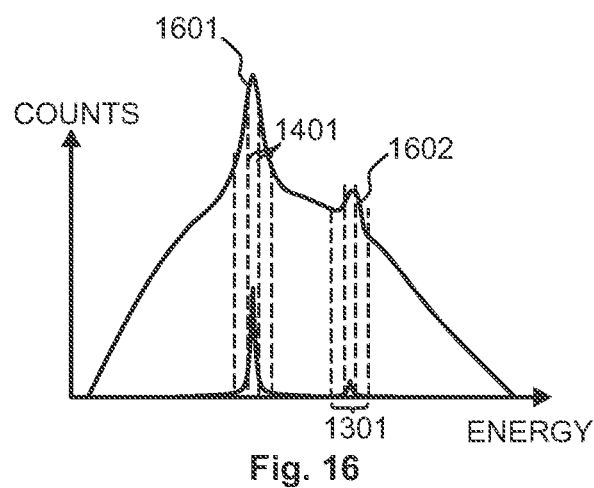
FIG. 16 illustrates example of radiation spectra.

FIG. 16 illustrates schematically a fluorescent X-ray spectrum that comprises two clear peaks 1601 and 1602. In such case the selected calculation method may depend on whether the peaks 1601 and 1602 both are characteristic peaks of the same element of interest, or whether one of them is a characteristic peak of some interfering element. The smaller peaks closer to the energy axis represent the estimated detection result that a detection channel equipped with a conventional (for example silicon dioxide) crystal would produce of these two peaks.

An interesting case is one where the peaks 1601 and 1602 both are peaks of the element of interest. Particularly interesting is if that one of them (here: peak 1601) is more intense, for the measuring of which the $SiO_2$-equipped detection channel is configured. In such a case the best features of both channels may come into use: the accurate wavelength selectivity of the silicon dioxide crystal can be used to separate a tightly defined wavelength range 1401 that only includes the desired characteristic peak, so that the relatively large intensity of that peak still gives a sufficient number of counts in the corresponding detector in a relatively short time. At the same time the good diffraction efficiency of the HOPG crystal can be used to separate a wider wavelength range 1301 that includes the other, lower characteristic peak. The concentration of the element of interest can be calculated from the detection results given by the two detectors, when the overall performance of the two detection channels is known from calibration measurements.

A method of the kind described above may be applicable in many cases where the characteristic fluorescent radiation comprises a K- or L-peak of an element with $30 \leq Z \leq 92$, where Z is the atomic number of said element. The flexible adaptability of the method suits well for measuring samples that comprise one or more elements of interest within a matrix consisting of primarily elements with $Z \leq 8$, where Z is the atomic number. This is the case of water-based slurries, for example.

The principles that have been discussed above concerning the use of two detection channels can be generalized to concern the use of three or more detection channels. The form factor of the detection channel that has been described above, i.e. the one in which each crystal diffractor 601 is enclosed in a casing delimited by a first planar surface 701 and a second planar surface 702 that is parallel to said first planar surface 701, enables distributing a plurality of detection channels as "cassettes" for example in a rotationally symmetric formation around the X-ray tube. Detection results from detection channels configured to detect characteristic fluorescent radiation of a same element can be combined in various ways as described above. The large number of detection channels allows calculating the concentrations of two or more elements of interest in the sample simultaneously, if the detection channels are configured to measure the characteristic fluorescent radiation of such two or more elements of interest. Cross-correlating the detection results from channels configured to detect different elements is also possible. For example if one element has two characteristic peaks, one of which is measured with a dedicated first detection channel while the other comes close to the characteristic peak of the other element of interest, the detection results from the first channel may be used to correct the detection results from that channel that is configured to measure the characteristic peak of the other element.

One factor to consider in the design of an industrial X-ray fluorescence analyzer for analyzing samples of slurry is the power of the X-ray tube, and the geometry and dimensioning of the area between the X-ray tube and the slurry handling unit.

Figure 17:
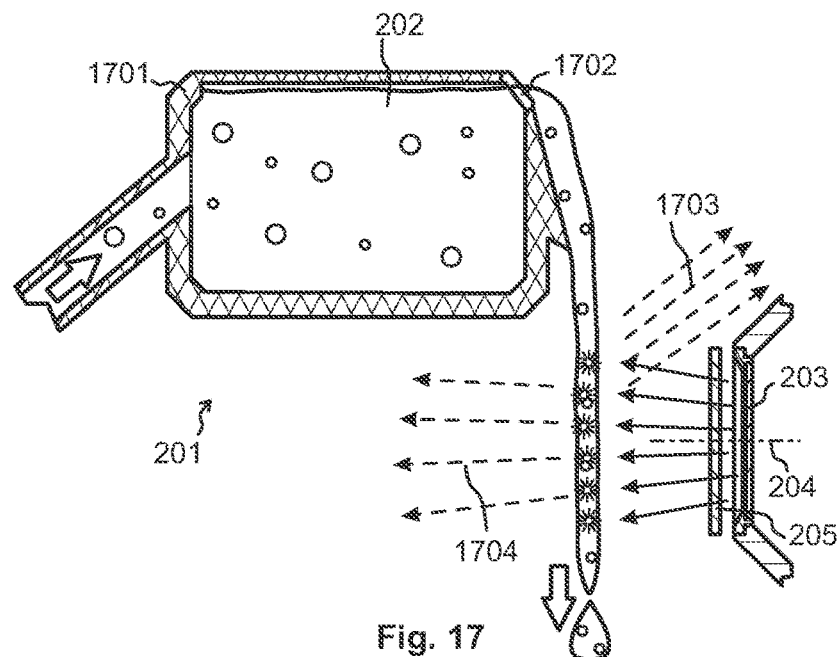
FIG. 17 illustrates an example of a slurry handling unit.

FIG. 17 illustrate the possibility of using so-called transmission geometry. The radiation window 203 of an X-ray tube is visible on the right in FIG. 17, and incident X-rays are emitted in the direction of the optical axis 204 through a primary filter plate 205. The slurry handling unit 201 comprises a chamber 1701 with an output slit 1702, from which the sample 202 flows out in a curtain-like form and falls downwards under the influence of gravity. The incident X-rays generate fluorescent X-rays in the relatively thin sheet of falling slurry. Reference designator 1703 points at fluorescent X-rays that are directed obliquely backwards, and that can be detected with detection channels (not shown in FIG. 17) placed much like in the geometries described earlier with reference to FIGS. 2, 3, 4, and 5. Reference designator 1704 points at fluorescent X-rays that are directed to other directions, particularly to directions that are on the other side of the sample flow. These can be detected with detection channels (not shown in FIG. 17) placed on that side. This may be a particularly advantageous way of placing detection channels, because they can get a better field of view and consequently a better spatial efficiency of collecting fluorescent X-rays. This may also help to bring the X-ray tube very close to the sample. It has to be noted, though, that proper radiation shielding geometrical precautions must be taken in order to prevent any of the incident X-rays from entering the detection channels.

Figure 18:
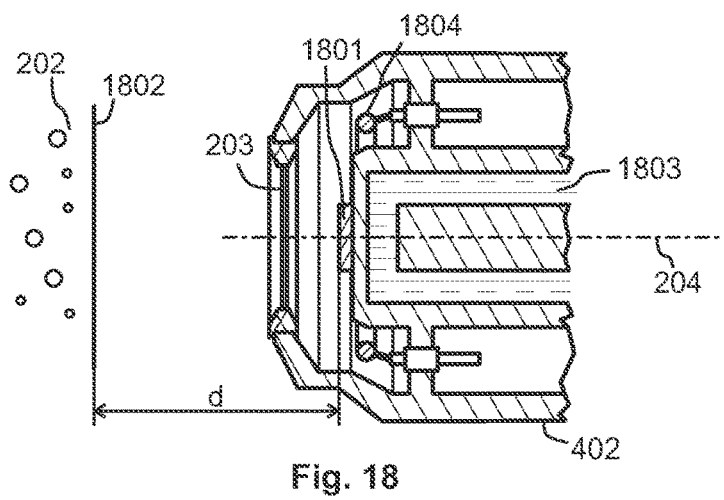
FIG. 18 illustrates an X-ray tube with its optical axis perpendicular against the sample surface.

FIG. 18 is a partial cross section of the output portion of an X-ray tube 402. The X-ray tube comprises an anode 1801 for generating the incident X-rays. The incident X-rays will be emitted in the direction of the optical axis 204 towards the sample 202, which here is shown only schematically without the slurry handling unit for reasons of graphical clarity. It is nevertheless assumed that the slurry handling unit is configured to maintain a planar surface 1802 of the sample 202 of slurry on a side facing the X-ray tube 402. As explained earlier, this can be accomplished for example by providing a sample window with a window foil made of a material that is transparent to X-rays. The sample window may be provided in a wall of a sample chamber, for allowing X-rays to pass through while keeping the sample of slurry within the sample chamber.

Other parts of the X-ray tube that are schematically shown in FIG. 18 are the circulation 1803 of cooling water, the ring-shaped cathode 1804 for emitting the accelerated electrons, and the radiation window 203.

When the aim is to produce so much fluorescent radiation that even very small concentrations of elements of interest could be detected, it is advantageous if as many photons (of sufficient energy) of the incident radiation as possible can be made to hit the sample 202. One way of achieving this is to have a very powerful X-ray tube. According to an embodiment the input power rating of the X-ray tube 402 is at least 400 watts. Even more powerful X-ray tubes can be used: according to other embodiments the input power rating of the X-ray tube 402 may be at least 1 kilowatt, or at least 2 kilowatts, or even at least 4 kilowatts. Even if only a fraction of the power that is announced as the input power rating of the X-ray tube will eventually come out in the form of generated incident X-rays, the input power rating is nevertheless an important indicator of the capability of the X-ray tube of producing an intense flux of incident X-rays.

Using X-ray tubes with higher power ratings than earlier means that radiation shielding must be reconsidered with respect to previously known, lower-powered X-ray sources. According to an embodiment, thicker radiation shielding plates and denser radiation shielding materials may be used to ensure that ionizing radiation does not leak into areas where it could be hazardous.

Another way of ensuring a very intense flux of incident X-rays hitting the sample 202 is to make the distance between the anode 1801 and the sample 202 as small as possible. The slurry handling unit may be configured to maintain a shortest linear distance d between the anode 1801 and the sample 202, so that d is shorter than 50 mm. In another embodiment d may be shorter than 40 mm. In another embodiment d may be shorter than 30 mm.

Figure 19:
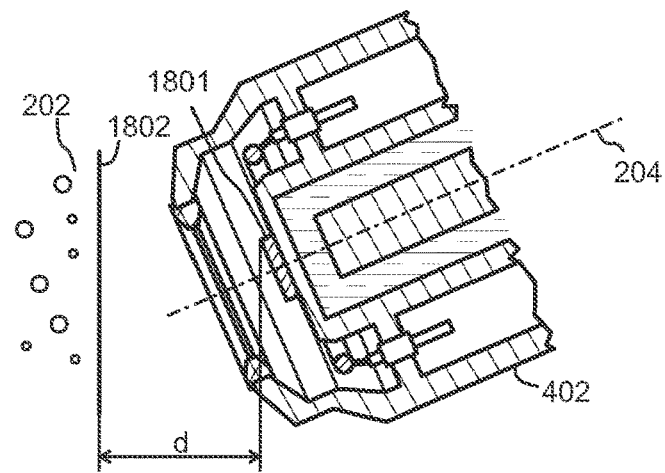
FIG. 19 illustrates an X-ray tube with its optical axis at an oblique angle against the sample surface.

It must be noted, however, that generally the closer the anode 1801 of the X-ray tube 402 is brought to the sample 202, the larger spatial angle around the sample 202 is blocked by the structures of the X-ray tube. This is an important factor to consider, because the structures of the X-ray tube 402 may block the field of view of the detection channels. One way to mitigate this problem is to use an X-ray tube of the so-called end window type, and not an X-ray tube of the side window type. FIGS. 18 and 19 can be considered to illustrate the use of an X-ray tube of the end window type. In an X-ray tube of this kind the radiation window 203 is generally at one end of a generally tubular structure, which leaves relatively much free space around said tubular structure for placing the detection channels. Another possibility would be to use an X-ray tube of the side window type, and to place the detection channels on one or two sides of the X-ray tube.

In all figures described so far, the optical path between the X-ray tube 402 and the sample 202 is also direct, which means that there are no diffractors therebetween. This is another way of ensuring that a maximum number of incident X-ray photons may hit the sample. First, the provision of a diffractor therebetween would inevitably mean a longer distance between the anode 1801 and the sample 202, because some space would need to be reserved for the diffractor. Second, the mere nature of a diffractor is to separate only a certain wavelength range from the original radiation spectrum, which would necessarily mean fewer incident X-ray photons hitting the sample. Other advantageous consequences of not using any so-called primary diffractor between the X-ray tube 402 and the sample 202 are the simultaneous provision of incident X-rays for exciting the characteristic peaks of a number of elements in the sample and that less structural parts are there that could block the field of view of the detection channels.

In FIG. 18 the optical axis 204 of the X-ray tube 402 is perpendicular against the planar surface 1802 of the sample 202. While this arrangement provides for excellent rotational symmetry for detection channels placed around the X-ray tube 402, it is not the only possibility. FIG. 19 illustrates an alternative embodiment, in which the optical axis 204 of the X-ray tube 402 is at an oblique angle against said planar surface. Such an arrangement may help to make the shortest linear distance d between the anode 1801 and the sample 202 even shorter, while simultaneously leaving sufficiently free field of view for detection channels on at least some sides of the X-ray tube 402. This principle is elaborated upon further in the following with reference to FIGS. 20 and 21.

Figure 20:
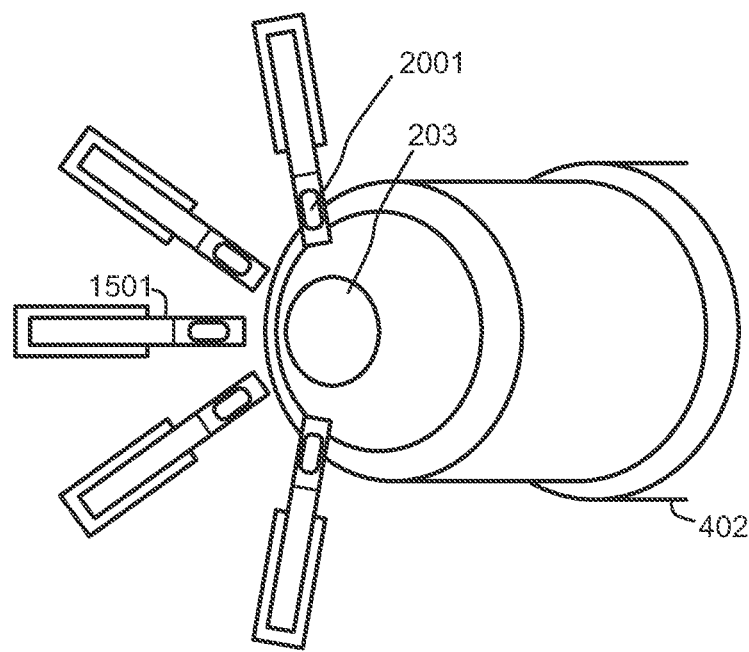
FIG. 20 illustrates an example of placing a plurality of detection channels.

FIG. 20 shows an X-ray tube 402 and five detection channels seen from the direction of the sample. The radiation window 203 of the X-ray tube 402 is visible in the middle of the drawing. The entry window of each detection channel for receiving fluorescent radiation is located in the proximal end face of the respective crystal diffractor; entry window 2001 is shown as an example. For the purpose of making as large proportion as possible of the generated fluorescent radiation enter a detection channel, it is advantageous to place these entry windows as close as possible to the sample, and also so that the entry window sees the sample surface in as large spatial angle as possible. Each of the plurality of crystal diffractors is located at a respective rotation angle around the optical axis of the X-ray tube 402. Each of said crystal diffractors is configured to separate a predefined wavelength range from fluorescent X-rays that propagate into the respective direction, and configured to direct the fluorescent X-rays in the respective separated predefined first wavelength range to a respective radiation detector.

Figure 21:
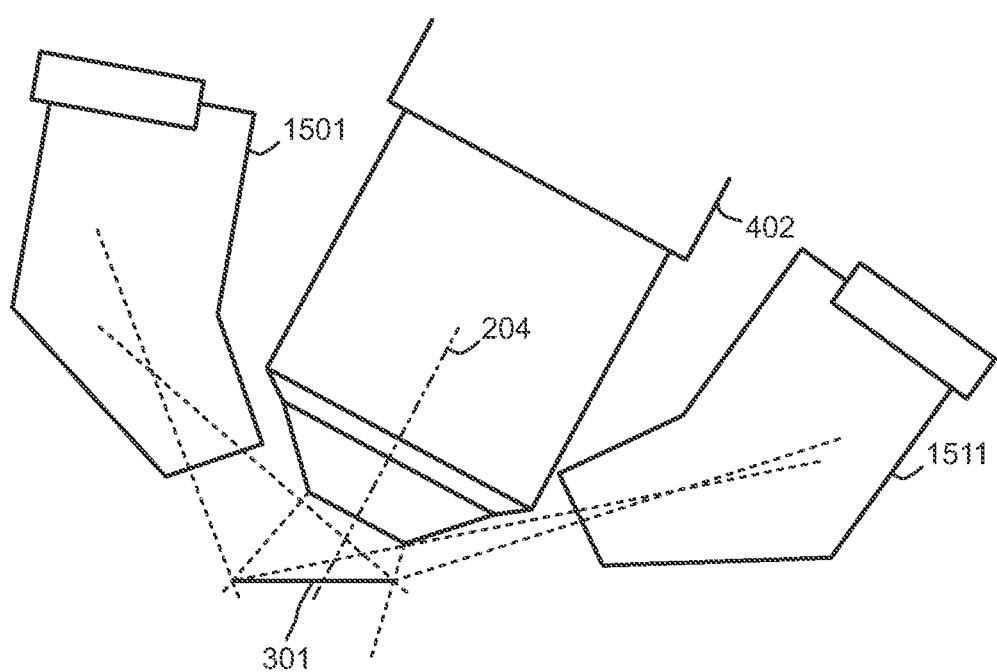
FIG. 21 illustrates an example of placing a plurality of detection channels.

FIG. 21 shows an X-ray tube 402 and two detection channels seen from the side. The sample window 301 is schematically shown in FIG. 21: this illustrates the area where the slurry handling unit is configured to maintain a planar surface of the sample of slurry on a side facing the X-ray tube 402. Thus this is the area that should be within the field of view of the X-ray tube 402 in order to make the incident X-rays hit the sample. This illustrates also the area that should cover as large spatial angle as possible in the field of view of the detection channels, in order to collect as much fluorescent X-rays as possible.

The optical axis 204 of the X-ray tube 402 is at an oblique angle against said planar surface. A first crystal diffractor 1501 is located at that rotational angle around said optical axis 204 at which said planar surface of said sample covers the largest portion of a field of view of the first crystal diffractor 1501. Assuming that no other structures block any part of the available field of view, in practice this means that the first crystal diffractor 1501 is located opposite to the X-ray tube, i.e. in the direction to which an imaginary light beam along the optical axis 204 would reflect if the sample surface was a mirror.

A second crystal diffractor 1511 is located at another rotational angle around said optical axis 204. In FIG. 21 the second crystal diffractor 1511 is located at what could be described as the worst possible rotational angle, because its view of the sample surface is limited by that edge of the X-ray tube 402 that comes closes to the sample window 301. If said other rotational angle differs by less than 180 degrees from that in which the first crystal diffractor 1501 is located, the second crystal diffractor 1511 could be located more like one of the plurality of other crystal diffractors in FIG. 20. In such a case the planar surface of the sample at the sample window 301 would cover a portion of the field of view of the second crystal diffractor 1511 that was between the two extremes shown in FIG. 21.

According to an embodiment, the first crystal diffractor 1501 that is placed at the optimal rotational angle (in terms of field of view) in FIGS. 20 and 21 is the one in which the diffractor crystal is a HOPG crystal and the radiation detector is a solid-state semiconductor detector. Taken the good diffraction efficiency of the HOPG crystal, such placing of the first crystal diffractor helps to ensure that a maximum number of fluorescent X-ray photons will eventually reach the detector. If there is some advance knowledge about the assumed levels of concentrations of various elements in the samples to be measured, it may be advantageous to place that crystal diffractor to the most optimal rotational angle that is configured to separate and direct to its respective detector the characteristic fluorescent radiation of that element of interest that is expected to have the smallest concentrations.

One factor to consider in the design of an industrial X-ray fluorescence analyzer for analyzing samples of slurry is the selection of radiation detectors in those channels that have diffractor crystals of other materials than pyrolytic graphite. The wavelength selectivity of conventional diffractor crystal materials such as silicon dioxide is relatively good, which can be interpreted so that there is not as much need for accurate energy resolution in the radiation detector as if a HOPG crystal was used. A gas-filled proportional counter may provide quite satisfactory detection results in a detection channel that has other than HOPG as the diffractor crystal, at an advantageously lower manufacturing cost than a solid-state semiconductor detector.

However, nothing in the foregoing should be interpreted against choosing a solid-state semiconductor detector also for detection channels that have other than HOPG as the diffractor crystal. Similarly it is not a mandatory requirement to use a solid-state semiconductor detector in the detection channel equipped with a HOPG crystal, if the energy resolution of another type of radiation detector is found to be sufficient.

FIGS. 22 to 25 illustrate calibration measurements, in which the vertical axis represents concentrations measured with one detection channel of a tested apparatus, which was an industrial X-ray fluorescence analyzer for analyzing samples of slurry according to an embodiment. The horizontal axis represents concentrations in the same samples but measured for prolonged periods with laboratory grade equipment, in order to as accurate and reliable results as possible. For the laboratory measurements the samples of slurry were dried and homogenized, and the amount of removed water was compensated for through calculation, in order to make the laboratory measurements comparable with the industrial-type measurements. If a calibration measurement of this kind shows the points settling along a straight line, the two different apparatuses give highly matching results, which means that the tested apparatus is very accurate. Deviations from a straight line show that the tested apparatus produces inaccurate results.

Figure 22:
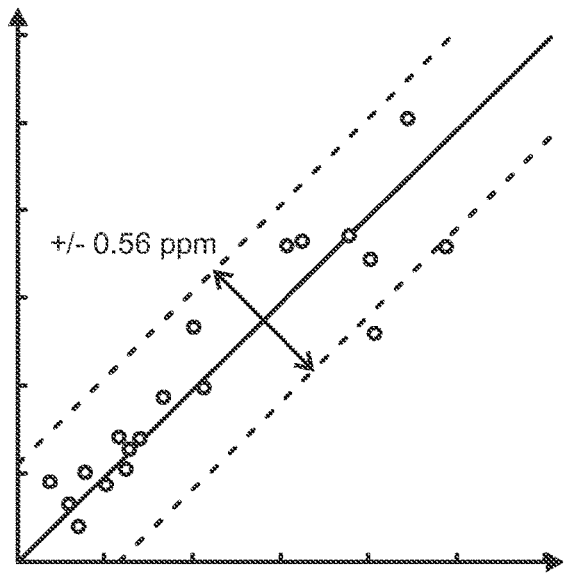
FIG. 22 illustrates measured detection accuracy of an example apparatus.
Figure 23:
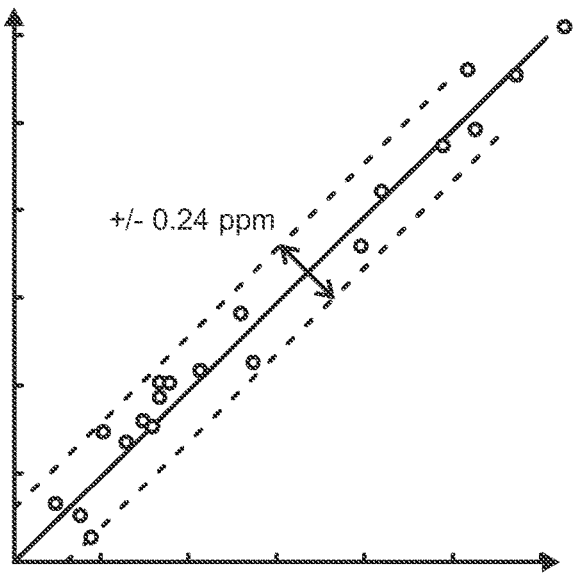
FIG. 23 illustrates measured detection accuracy of an example apparatus.
Figure 24:
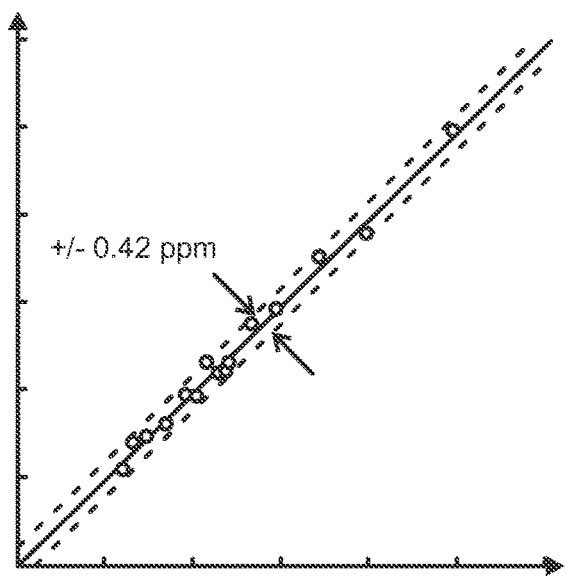
FIG. 24 illustrates measured detection accuracy of an example apparatus.
Figure 25:
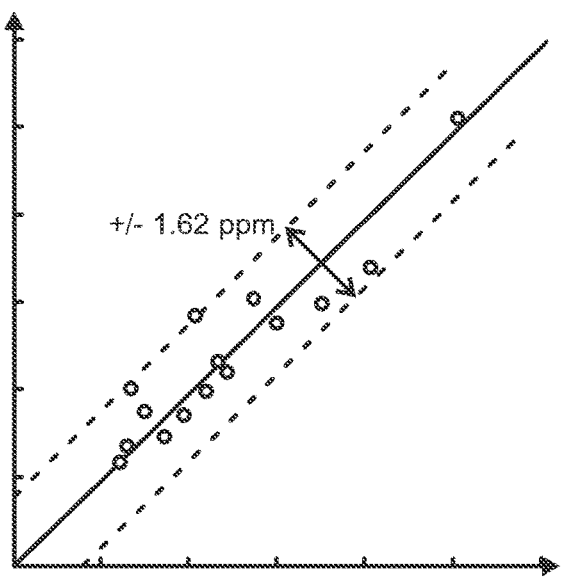
FIG. 25 illustrates measured detection accuracy of an example apparatus.

The scales are arbitrary, but the scales in FIGS. 22 and 23 are the same, and the scales in FIGS. 24 and 25 are the same. The element of interest was gold in all measurements. FIGS. 22 and 23 represent measurements of samples in which the concentration of an interfering element was below 300 ppm, while the measurements of FIGS. 24 and 25 its concentration varied between 0 and 2%. An interfering element is one that has a characteristic fluorescent peak close to at least one characteristic fluorescent peak of the element of interest.

FIGS. 22 and 24 represent cases in which the measurement with the tested apparatus was made using a detection channel that had a silicon dioxide crystal in the crystal diffractor and a gas-filled proportional counter as the radiation detector. FIGS. 23 and 25 represent cases in which the measurement with the tested apparatus was made using a detection channel that had a HOPG crystal in the crystal diffractor and a solid-state semiconductor detector as the radiation detector.

A comparison of FIGS. 22 and 23 shows that when the concentration of an interfering element is small, the detection channel with a HOPG crystal and a solid-state semiconductor detector gives more accurate detection results than the detection channel with a silicon dioxide crystal and a gas-filled proportional counter. The average error between concentrations measured with the HOPG channel of the tested apparatus and those measured in laboratory was +/−0.24 ppm, while the comparable average error with a silicon dioxide crystal and a gas-filled proportional counter was +/−0.56 ppm.

A comparison of FIGS. 24 and 25 shows that when the concentration of an interfering element is significant, the detection channel with a HOPG crystal and a solid-state semiconductor detector gives less accurate detection results than the detection channel with a silicon dioxide crystal and a gas-filled proportional counter. The average error between concentrations measured with the HOPG channel of the tested apparatus and those measured in laboratory was +/−1.62 ppm, while the comparable average error with a silicon dioxide crystal and a gas-filled proportional counter was +/−0.42 ppm.

The results shown in FIGS. 22 to 25 can be utilized in many ways. For example, the industrial X-ray fluorescence analyzer for analyzing samples of slurry may be equipped with first, second, and third detection channels, of which the first and second detection channels are both equipped with crystal diffractors configured to separate and direct to their respective detectors characteristic fluorescent X-rays of the same element, like gold. The first detection channel may be one with a HOPG crystal and a solid-state semiconductor detector, and the second detection channel may be one with a silicon dioxide crystal and a gas-filled proportional counter. The third detection channel may be equipped with a crystal diffractor configured to separate and direct to its respective detector characteristic fluorescent X-rays of an interfering element. The detection results of all three detection channels can be then analyzed. If the detection results produced by the third detection channel show there to be a significant concentration of the interfering element in the sample, the calculation of the concentration of gold would emphasize more (or even use exclusively) the detection results of the second detection channel. Correspondingly if the detection results produced by the third detection channel show there to be only an insignificant concentration of the interfering element in the sample, the calculation of the concentration of gold would emphasize more (or even use exclusively) the detection results of the first detection channel.

Many advantageous features of the industrial X-ray fluorescence analyzer for analyzing samples of slurry have been described above. In the end they all serve a common purpose, which is to make reliable measurements of even very small concentrations of elements of interest in slurries of various kinds, at reasonable cost and under the harsh conditions that an industrial environment may place: short measurement times; extreme temperatures; frequent occurrence of humidity, dust, and dirt; long intervals between servicing; and the like. The advantageous features may be combined with each other in numerous ways, so that the most advantageous combination may depend on a particular case and its specific boundary conditions.

It is obvious to a person skilled in the art that with the advancement of technology, the basic idea of the invention may be implemented in various ways. The invention and its embodiments are thus not limited to the examples described above, instead they may vary within the scope of the claims. As an example, even of gold has been frequently mentioned above as a typical element of interest, the same principles are applicable also to measurements of other elements of interest. Examples of such other elements of interest are for example copper, silver, metals of the platinum group, and uranium.

The invention claimed is:

1. An X-ray fluorescence analyzer, comprising:
an X-ray tube for emitting incident X-rays in the direction of a first optical axis,
a slurry handling unit configured to maintain a constant distance between a sample of slurry and said X-ray tube,
a first crystal diffractor located in a first direction from said slurry handling unit, said first crystal diffractor being configured to separate a predefined first wavelength range from fluorescent X-rays that propagate into said first direction, and configured to direct the fluorescent X-rays in the separated predefined first wavelength range to a first radiation detector, wherein:
the first crystal diffractor comprises a pyrolytic graphite crystal that has a diffractive surface, and
said first radiation detector is a solid-state semiconductor detector;
characterized in that
the diffractive surface of said pyrolytic graphite crystal is a simply connected surface; and
the crystal is the wavelength-dispersive component of the crystal diffractor.

2. The X-ray fluorescence analyzer according to claim 1, wherein the diffractive surface of said pyrolytic graphite crystal is curved in one direction only.

3. The X-ray fluorescence analyzer according to claim 1, wherein the first crystal diffractor comprises a substrate to which said pyrolytic graphite crystal is attached, and wherein a three-dimensional geometrical shape of the entity constituted by said pyrolytic graphite crystal and said substrate is that of a prism, one side face of which is cut away by the curved diffractive surface.

4. The X-ray fluorescence analyzer according to claim 1, wherein said first radiation detector is one of: a PIN di-ode detector, a silicon drift detector, a germanium detector, a germanium drift detector.

5. The X-ray fluorescence analyzer according to claim 1, wherein the first crystal diffractor comprises:
a first slit on a first optical path between said slurry handling unit and said pyrolytic graphite crystal, and
a second optical path between said pyrolytic graphite crystal and said first radiation detector.

6. The X-ray fluorescence analyzer according to claim 5, wherein:
the diffractive surface of said pyrolytic graphite crystal is curved in one direction only, with a radius of curvature in a plane defined by said first and second optical paths, and
said first slit is a linear slit oriented perpendicular against said plane.

7. The X-ray fluorescence analyzer according to claim 5, wherein:
the diffractive surface of said pyrolytic graphite crystal is curved in two directions, forming a part of a toroidal surface, and
said first slit is a curved slit with a first radius of curvature oriented perpendicular against said first optical path.

8. The X-ray fluorescence analyzer according to claim 5, wherein:
the diffractive surface of said pyrolytic graphite crystal is curved in two directions, forming a part of a rotationally symmetric surface, the rotational axis of which is in the plane defined by said first and second optical paths, and
said first slit is point-like.

9. The X-ray fluorescence analyzer according to claim 6, wherein:
the first crystal diffractor comprises a second slit on said second optical path between said pyrolytic graphite crystal and said first radiation detector,
a center point of said diffractive surface, said first slit, and said second slit are located on a Rowland circle the radius of which is R,
a radius of curvature of said diffractive surface in the plane defined by said first and second optical paths is 2R, and
a radius of curvature of reticular planes in said crystal is 2R; so that the first crystal diffractor has a Johann geometry.

10. The X-ray fluorescence analyzer according to claim 6, wherein:
the first crystal diffractor comprises a second slit on said second optical path between said pyrolytic graphite crystal and said first radiation detector,
a center point of said diffractive surface, said first slit, and said second slit are located on a Rowland circle the radius of which is R,
a radius of curvature of said diffractive surface in the plane defined by said first and second optical paths is R, and
the radius of curvature of reticular planes in said crystal is 2R; so that the first crystal diffractor has a Johansson geometry.

11. The X-ray fluorescence analyzer according to claim 9, wherein R is at most 40 centimeters.

12. The X-ray fluorescence analyzer according to claim 6, wherein:
said first crystal diffractor is enclosed in a casing delimited by a first planar surface and a second planar surface that is parallel to said first planar surface.

13. The X-ray fluorescence analyzer according to claim 6, comprising a plurality of other crystal diffractors in addition to said first crystal diffractor, each of said first and other crystal diffractors being located at a respective rotation angle around said first optical axis and each of said first and other crystal diffractors being configured to separate a predefined wavelength range from fluorescent X-rays that propagate into the respective direction, and configured to direct the fluorescent X-rays in the respective separated predefined wavelength range to a respective radiation detector.

14. The X-ray fluorescence analyzer according to claim 13, wherein:
said plurality of other crystal diffractors comprises a second crystal diffractor comprising a second crystal, configured to direct the fluorescent X-rays in the respective separated second predefined wavelength range to a respective second radiation detector,
said second crystal is of a material other than pyrolytic graphite, and said first and second crystal diffractors are con-figured to direct to their respective radiation detectors characteristic fluorescent radiation of a same element.

15. The X-ray fluorescence analyzer according to claim 14, wherein said second crystal is one of: a silicon dioxide crystal, a lithium fluoride crystal, an ammonium dihydrogen phosphate crystal, a potassium hydrogen phthalate crystal.

16. The X-ray fluorescence analyzer according to claim 14, wherein said second radiation detector is a gas-filled proportional counter.

17. The X-ray fluorescence analyzer according to claim 14, wherein said element is gold.

18. The X-ray fluorescence analyzer according to claim 14, wherein:
said slurry handling unit is configured to maintain a planar surface of said sample of slurry on a side facing said X-ray tube,
said first optical axis is at an oblique angle against said planar surface,
said first crystal diffractor is located at that rotational angle around said first optical axis at which said planar surface of said sample covers the largest portion of a field of view of the first crystal diffractor, and
said second crystal diffractor is located at another rotational angle around said first optical axis.

19. The X-ray fluorescence analyzer according to claim 6, wherein an energy resolution of said first radiation detector is better than 300 eV at a reference energy of 5.9 keV.

20. The X-ray fluorescence analyzer according to claim 6, wherein the in-put power rating of said X-ray tube is at least 400 watts.

21. The X-ray fluorescence analyzer according to claim 20, wherein the input power rating of said X-ray tube is at least 1 kilowatt, preferably at least 2 kilowatts, and more preferably at least 4 kilowatts.

22. The X-ray fluorescence analyzer according to claim 6, wherein the optical path between said X-ray tube and said slurry handling unit is direct with no diffractor therebetween.

23. The X-ray fluorescence analyzer according to claim 6, wherein
the X-ray tube comprises an anode for generating said incident X-rays, and
said slurry handling unit is configured to maintain a shortest linear distance that is shorter than 50 mm, preferably shorter than 40 mm, and more preferably shorter than 30 mm between said sample of slurry and said anode.

24. The X-ray fluorescence analyzer according to claim 23, wherein said X-ray tube is an X-ray tube of the end window type.

25. The X-ray fluorescence analyzer according to claim 6, further comprising:
an analyzer body,
a front wall of said analyzer body,
an opening in said front wall, and
a holder for removably holding said slurry handling unit against an outer side of said front wall and aligned with said opening in said front wall.

26. The X-ray fluorescence analyzer according to claim 25, wherein said X-ray tube and said first crystal diffractor are both inside said analyzer body, on the same side of said front wall.

27. The X-ray fluorescence analyzer according to claim 6, comprising a filter plate on the optical path between said X-ray tube and said slurry handling unit.

28. The X-ray fluorescence analyzer according to claim 27, wherein said filter plate is located closer to said X-ray tube than to said slurry handling unit.

29. The X-ray fluorescence analyzer according to claim 6, comprising a calibrator plate and an actuator configured to controllably move said calibrator plate between at least two positions, of which a first position is not on the path of the incident X-rays and a second position is on the path of the incident X-rays and in a field of view of the first crystal diffractor.

* * * * *